United States Patent
Blankenberg

(10) Patent No.: US 11,253,568 B2
(45) Date of Patent: Feb. 22, 2022

(54) USE OF ANNEXIN V AS A METHOD TO BLOCK TUMOR INDUCED IMMUNOSUPPRESSION OF THE INNATE IMMUNE RESPONSE

(71) Applicant: The Board of Trustees of the Leland Stanford Junior University, Stanford, CA (US)

(72) Inventor: Francis G. Blankenberg, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 369 days.

(21) Appl. No.: 15/515,033

(22) PCT Filed: Oct. 2, 2015

(86) PCT No.: PCT/US2015/053828
§ 371 (c)(1),
(2) Date: Mar. 28, 2017

(87) PCT Pub. No.: WO2016/054574
PCT Pub. Date: Apr. 7, 2016

(65) Prior Publication Data
US 2017/0202914 A1 Jul. 20, 2017

Related U.S. Application Data

(60) Provisional application No. 62/059,669, filed on Oct. 3, 2014.

(51) Int. Cl.
| | | |
|---|---|---|
| *A61K 45/06* | (2006.01) | |
| *A61P 35/00* | (2006.01) | |
| *A61K 38/17* | (2006.01) | |
| *A61K 9/00* | (2006.01) | |

(52) U.S. Cl.
CPC ........ *A61K 38/1709* (2013.01); *A61K 9/0019* (2013.01); *A61K 45/06* (2013.01)

(58) Field of Classification Search
CPC ... A61K 38/1709; A61K 9/0019; A61K 45/06

USPC ........................................................ 514/19.3
See application file for complete search history.

(56) References Cited

U.S. PATENT DOCUMENTS

| | | |
|---|---|---|
| 2004/0096467 A1 | 5/2004 | Kalden |
| 2006/0211611 A1 | 9/2006 | Coleman |
| 2006/0293226 A1 | 12/2006 | Bertling |
| 2008/0069823 A1 | 3/2008 | Allison |
| 2009/0191121 A1 | 7/2009 | Thorpe et al. |

FOREIGN PATENT DOCUMENTS

| | | |
|---|---|---|
| WO | 2003/022883 A2 | 3/2003 |
| WO | 2004/064855 A1 | 8/2004 |
| WO | 2010/149394 A1 | 12/2010 |

OTHER PUBLICATIONS

Mellman et al., "Cancer immunotherapy comes of age", Nature, Dec. 21, 2011, pp. 480-489, vol. 480, Macmillan Publishers Limited, London, United Kingdom.
Rosenberg, "Raising the Bar: The Curative Potential of Human Cancer Immunotherapy", Science Translational Medicine, Mar. 28, 2012, pp. 1-5. vol. 4, Issue 127, (127ps8), American Association for the Advancement of Science, Washington, D.C.
Callahan et al., "At the Bedside: CTLA-4- and PD-1-blocking antibodies in cancer immunotherapy", Journal of Leukocyte Biology, Jul. 1, 2013, vol. 94, No. 1, Wiley, Hoboken, NJ.
Kasikara et al., "Phosphatidylserine Sensing by TAM Receptors Regulates AKT-Dependent Chemoresistance and PD-L1 Expression", Molecular Cancer Research, Feb. 9, 2017, pp. 753-764, vol. 15, Issue 6, American Association for Cancer Research, Philadelphia, PA.
Callahan et al. (2013) At the bedside: CTLA-4- and PD-1-blocking antibodies in cancer immunotherapy, Journal of Leukocyte Biology, vol. 94, No. 1, p. 41-53.
Yan X et al. (2012) Annexin-V promotes anti-tumor immunity and inhibits neuroblastoma growth in vivo. Cancer Immunology, Immunotherapy, vol. 61, No. 11, p. 1917-1927.

*Primary Examiner* — Yan Xiao
(74) *Attorney, Agent, or Firm* — Pamela J. Sherwood; Bozicevic, Field & Francis LLP

(57) ABSTRACT

Methods are provided for treating a subject with cancer, with a therapeutic dose of annexin V to the subject.

13 Claims, 7 Drawing Sheets

USE OF ANNEXIN V AS A METHOD TO BLOCK TUMOR INDUCED IMMUNOSUPPRESSION OF THE INNATE IMMUNE RESPONSE

CROSS REFERENCE

This is a 371 application and claims the benefit of PCT Application No. PCT/US2015/053828, filed Oct. 2, 2015, which claims benefit of U.S. Provisional Patent Application No. 62/059,669, filed Oct. 3, 2015, which applications are incorporated herein by reference in their entirety.

BACKGROUND

Cancer, also known as malignant neoplasm, is characterized by an abnormal growth of cells that display uncontrolled cell division, invasion and destruction of adjacent tissues, and sometimes metastasis to other locations in the body. There are more than 100 types of cancer, including breast cancer, skin cancer, lung cancer, colon cancer, prostate cancer, and lymphoma. Cancer is the second leading cause of death in America and it causes about 13% of all deaths. Cancer may affect people at all ages, even fetuses, but the risk for most types of cancer increases with age.

Tumor immunoevasion is an advanced phase of cancer immunosurveillance in which tumor cells acquire the ability to circumvent host immune systems and exploit protumorigenic inflammation. The interaction between tumor cells and host immune cells plays an important role in multiple stages of tumorigenesis, and evidence suggests that host immune responses are a factor in the clinical outcome of cancer patients. Manipulation of the endogenous immune system has emerged as an effective anticancer therapy in patients with advanced cancer. (Mellman et al. (2011) Nature 480: 480-489; Rosenberg (2012) Sci Transl Med 4: 127ps8).

The tumor microenvironment has a significant impact on the functional properties of immunoregulatory components that regulate whether host responses promote or antagonize tumor growth. Tumor cells and tumor-infiltrating lymphocytes adopt strategies to evade antitumor processes and may enhance the metastatic potential through the activation of chronic inflammatory signals. The innate and adaptive immune systems play a critical role in detecting and eliminating transformed cells by activating multiple sets of myeloid cells and lymphocytes. Tumor-infiltrating immune cells also contribute to tumor progression by triggering tumor angiogenesis and immune suppression.

Tumor immunoevasion has multiple impacts on tumorigenesis by triggering tolerogenic responses to tumor cells and by exploiting pro-tumor inflammation. Phosphatidylserine (PS) is a constitutive anionic plasma membrane phospholipid selectively exposed on the surface of apoptotic or stressed cells. Its presence is widely believed to be an "eat me signal", through which the innate immune system, including NK cells, T-cells and monocytes/macrophages recognize and remove target cells. However it has also been observed that contact with PS expressing tumor cells strongly activates immunosuppressive regulatory T-cells, and thus may provide a mechanism by which tumor cells evade recognition by the immune system.

Biological therapies hold tremendous potential for the treatment of cancers, yet there still exists a need for a therapy that provides for effective killing of tumor cells through endogenous biological systems. The present invention addresses this need.

SUMMARY OF THE INVENTION

Methods are provided for treatment of cancer by administering an effective dose of an agent that blocking the binding sites of phosphatidylserine (PS) on tumor cells. In some embodiments the blocking agent is a protein that binds to PS, thereby competitively blocking the available binding sites. Polypeptides of interest include, without limitation, annexin V protein and PS binding fragments derived therefrom, and include wild-type and mutant (e.g. annexin V-128) sequences. Annexin V protein is of particular interest.

In some embodiments of the invention, an effective dose of annexin V protein is administered, e.g. by parenteral administration, locally or systemically to an individual with cancer, where cancers include, without limitation carcinomas, sarcomas, lymphomas, leukemias, gliomas, melanomas, etc. In some embodiments the administration is performed by continuous systemic infusion. In some embodiments such continuous systemic infusion comprises intraperitoneal infusion. In some embodiments, an osmotic pump is deployed. In some embodiments the cancer is a solid tumor, including without limitation carcinomas.

Without being bound by any theory, the subject methods indicate that exogenously administered annexin V has an anti-tumor effect through the binding of PS on tumor cells, thereby blocking T-reg immunosuppression of the immune system. Local immunosuppression via PS expression is a feature of many tumors including aggressive forms of breast cancer (triple negative), neuroblastoma, and head and neck cancer. The methods of the invention provide a well-tolerated blockade of PS, that enhances host immune response to tumor.

In some embodiments of the invention, an effective dose of annexin V protein is administered parenterally to an individual diagnosed with cancer, where the administration may be intra-tumoral, i.v., i.p., or the like, in particular intraperitoneal continuous infusion. The effective dose in a human may be up to about 50 µg/kg, up to about 100 µg/kg, up to about 250 µg/kg, up to about 500 µg/kg, up to about 750 µg/kg, up to about 1 mg/kg, up to about 1.5 mg/kg, up to about 2 mg/kg, up to about 5 mg/kg, up to about 7.5 mg/kg, up to about 10 mg/kg, up to about 20 mg/kg.

The effective dose of annexin V may be combined with other treatment modalities, including without limitation chemotherapeutic drugs, radiation therapy, anti-cancer biologic agents such as monoclonal antibodies directed to tumor antigens, VEGF, etc.; and the like. In some embodiments a synergistic effect is observed when the annexin V therapy is combined with an anti-cancer biologic agent. In some embodiments, the biologic agent is an antibody that specifically binds to a "checkpoint inhibitor". In other embodiments, the treatment modality is radiation, which may be locally administered.

In some embodiments, the Annexin V protein is administered in a manner that provides for prolonged blood clearance of the protein, for example where the half-life of the protein in circulation is at least about 30 minutes, at least about 1 hour, at least about 1.5 hours, at least about 2 hours, at least about 2.5 hours, at least about 3 hours or more. In some embodiments the manner of administration is intraperitoneal injection, or osmotic pump. In other embodiments the route of administration is intra-venous injection over an extended period of time, for example where a daily dosage as described above is delivered over a period of up to 30 minutes, up to one hour, up to 2 hours, up to 4 hours, up to 6 hours, up to 8 hours, up to 12 hours, up to 16 hours, up to 24 hours.

In some embodiments of the invention, the presence of excess PS on cancer cells is imaged with an annexin V reagent, where an individual with a tumor positive for expression of surface PS is then selected for treatment with the methods of the invention. In some embodiments of the invention, the presence of cancer stem cells expressing surface PS is determined prior to treatment. The methods of the invention also find use in blocking immunosuppression induced by cancer stem cells. Stem cells also express levels of PS to avoid immune-recognition and therefore can also be treated with annexin V.

Another aspect of the present invention relates to the use of an annexin V agent in the manufacture of a medicament to stabilize, prevent or reduce tumor growth, including methods of reducing the growth of cancer stem cells. The medicament may be administered to an individual diagnosed with PS positive cancer cells.

Still another aspect of the present invention provides a kit to stabilize, prevent or reduce tumor growth. The kit includes a therapeutic annexin V agent, which blocks PS on the surface of cancer cells, including cancer stem cells, in an amount sufficient to stabilize, prevent or reduce disease. The kit may also include reagents for phenotyping cancers for cell surface expression of PS. The kit may also instructions for use, reagents for monitoring cancer, and the like.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
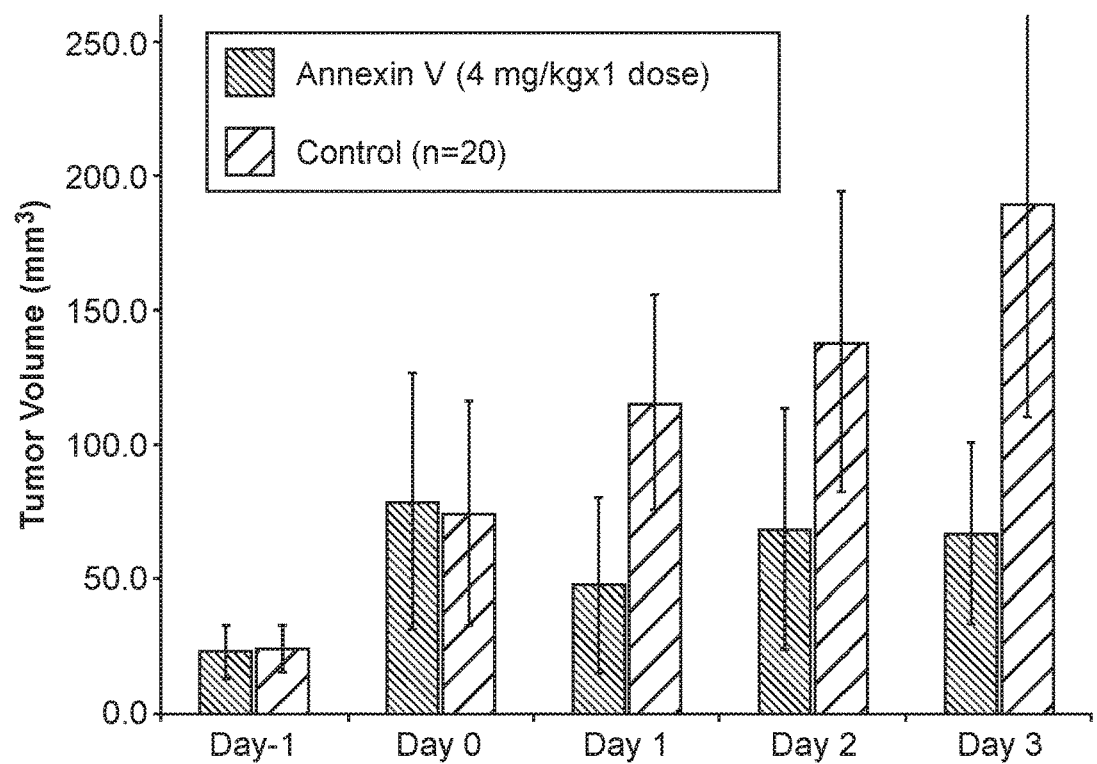
FIG. 1 illustrates the change in tumor size in animals treated with annexin V, versus a control group.
Figure 1:
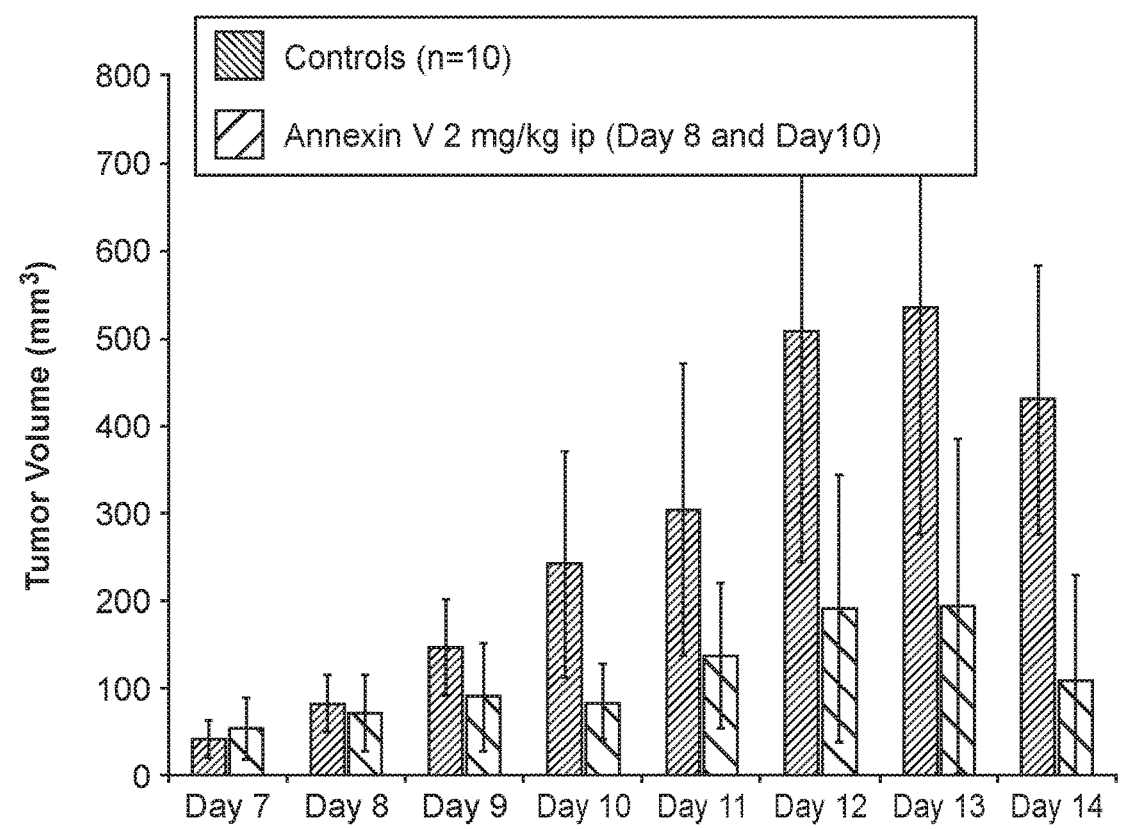

The invention provides methods for treating cancer. The methods of the invention comprise administering to the subject an effective amount of an agent that provides annexin V binding activity, to suppress or prevent initiation, progression, or relapses of disease. In this invention, administering the instant compositions can be effected or performed using any of the various methods and delivery systems known to those skilled in the art. The administering can be performed, for example, intravenously, via implant, transmucosally, transdermally, intramuscularly, intrathecally, and subcutaneously. The delivery systems described below, which employ a number of routinely used pharmaceutical carriers, are only representative of the many embodiments envisioned for administering the annexin V compositions.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development; or (c) relieving the disease symptom(s), i.e., causing regression of the disease and/or symptom(s). Those in need of treatment include those already inflicted (e.g., those with cancer, those with an infection, etc.) as well as those in which prevention is desired (e.g., those with increased susceptibility to cancer, those with an increased likelihood of infection, those suspected of having cancer, those suspected of harboring an infection, etc.).

A therapeutic treatment is one in which the subject is afflicted prior to administration and a prophylactic treatment is one in which the subject is not afflicted prior to administration. In some embodiments, the subject has an increased likelihood of becoming afflicted or is suspected of being inflicted prior to treatment. In some embodiments, the subject is suspected of having an increased likelihood of becoming afflicted.

"Comparable cell" shall mean a cell whose type is identical to that of another cell to which it is compared. Examples of comparable cells are cells from the same cell line.

"Specifically inhibit" the expression of a protein shall mean to inhibit that protein's expression (a) more than the expression of any other protein, or (b) more than the expression of all but 10 or fewer other proteins.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function.

In one embodiment, the term "suitable conditions" as used herein means physiological conditions.

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. Preferably, the mammal is human.

A "therapeutically effective dose" or "therapeutic dose" is an amount sufficient to effect desired clinical results (i.e., achieve therapeutic efficacy). A therapeutically effective dose can be administered in one or more administrations. For purposes of this invention, a therapeutically effective dose of Annexin V is an amount that is sufficient to palliate, ameliorate, stabilize, reverse, prevent, slow or delay the progression of the disease state (e.g., cancer) by increasing innate immune responsiveness. Thus, a therapeutically effective dose of Annexin V agent reduces the binding of phosphatidylserine on an cancer cell to an immune cells, e.g. a regulatory T cell, a phagocytic cells, an NK cell, and the like, at an effective dose for increasing direct or phagocytic killing of the cancer cell.

The terms "specific binding," "specifically binds," and the like, refer to non-covalent or covalent preferential binding to a molecule relative to other molecules or moieties in a solution or reaction mixture (e.g., annexin V specifically binds to phosphatidylserine). In some embodiments, the affinity of one molecule for another molecule to which it specifically binds is characterized by a $K_D$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{13}$ M or less, $10^{-14}$ M or less, $10^{-15}$ M or less, or $10^{-16}$ M or less). "Affinity" refers to the strength of binding, increased binding affinity being correlated with a lower $K_D$.

The term "specific binding member" as used herein refers to a member of a specific binding pair (i.e., two molecules, usually two different molecules, where one of the molecules, e.g., a first specific binding member, through non-covalent means specifically binds to the other molecule, e.g., a second specific binding member).

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "sample" with respect to a patient encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample comprising target cells or normal control cells or suspected of comprising such cells or biological fluids derived therefrom (e.g., cancerous cell, infected cell, etc.), e.g., a sample comprising polynucleotides and/or polypeptides that is obtained from such cells (e.g., a cell lysate or other cell extract comprising polynucleotides and/or polypeptides). A biological sample comprising an inflicted cell from a patient can also include non-inflicted cells.

Annexin-V (PAP-I, lipocortin-V) acts as a potent anticoagulant by binding to negatively charged phospholipids with high affinity, for example having a Kd in the $10^{-9}$ to $10^{-10}$ M range. Annexin V forms a shield around negatively-charged phospholipid molecules. The formation of blocks the entry of phospholipids into coagulation (clotting) reactions, and prevents interaction of the phospholipid with immunoregulatory cells. The genetic sequence of human annexin V can be accessed at Genbank, NM_001154. The crystal and molecular structure is described in Romisch and Paques (1992) J. Mol. Biol. 223 (3), 683-704. Annexin V polypeptides or biologically active fragments and variants thereof, and the like, are used in the treatment of cancer. In some embodiments the annexin V has a wild-type or native sequence. In other embodiments the annexin V is a annexin V-128 mutant protein.

Active fragments of annexin V share a functional or binding property with full length annexin V. Epitopic fragments of annexin V bind to a monoclonal antibody that binds to full length annexin V. "Activity" of annexin V shall mean any binding function performed by that protein.

Annexin V polypeptides, which can be used in the methods of the invention, comprise at least about 50 contiguous amino acids, usually at least about 100 contiguous amino acids, at least about 150 contiguous amino acids, at least about 200 contiguous amino acids, at least about 250 contiguous amino acids, and which may include up to 320 contiguous amino acids of an annexin V protein, including without limitation human annexin V protein, or modifications thereof, and may further include fusion polypeptides as known in the art in addition to the provided sequences. The Annexin V sequence may be from any mammalian or avian species, e.g. primate sp., particularly humans; rodents, including mice, rats and hamsters; rabbits; equines, bovines, canines, felines; etc. Of particular interest are the human proteins.

In some embodiments of the invention, the annexin V protein, or a functional fragment thereof is administered to a patient. Annexin V polypeptides useful in this invention also include derivatives, variants, and biologically active fragments of naturally occurring annexin V polypeptides, and the like. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%.

The sequence of annexin V peptides as described above may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The proteins may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated, where the polyethyleneoxy group provides for enhanced lifetime in the blood stream. The peptides may also be combined with other proteins in a fusion protein, typically where the two proteins are not normally joined, such as the Fc of an IgG isotype, which may be complement binding, with a toxin, such as ricin, abrin, diphtheria toxin, or the like, or with specific binding agents that allow targeting to specific moieties on a target cell.

The annexin V may be fused to another polypeptide to provide for added functionality, e.g. to increase the in vivo stability. Generally such fusion partners are a stable plasma protein, which may, for example, extend the in vivo plasma half-life of the Annexin V when present as a fusion, in particular wherein such a stable plasma protein is an immunoglobulin constant domain.

The annexin V for use in the subject methods may be produced from eukaryotic or prokaryotic cells, or may be synthesized in vitro. Where the protein is produced by prokaryotic cells, it may be further processed by unfolding, e.g. heat denaturation, DTT reduction, etc. and may be further refolded, using methods known in the art. By using synthesizers, naturally occurring amino acids may be substituted with unnatural amino acids. The particular sequence and the manner of preparation will be determined by convenience, economics, purity required, and the like.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one embodiment of the invention, the Annexin V polypeptide consists essentially of a polypeptide sequence of around about 320 amino acids in length and having a sequence of an Annexin V peptide as described above. By "consisting essentially of" in the context of a polypeptide described herein, it is meant that the polypeptide is composed of the Annexin V sequence, which sequence is optionally flanked by one or more amino acid or other residues that do not materially affect the basic characteristic(s) of the polypeptide.

As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD 80 and CD86; and PDI with its ligands PDLI and PDL2 (Pardoll, Nature Reviews Cancer 12: 252-264, 2012). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies.

As used herein, the term "antibody" includes reference to both glycosylated and non-glycosylated immunoglobulins of any isotype or subclass or to an antigen-binding region thereof that competes with the intact antibody for specific binding, unless otherwise specified, including monoclonal antibodies, bispecific antibodies, minibodies, domain antibodies, synthetic antibodies, antibody mimetics, chimeric antibodies, humanized antibodies, human antibodies, antibody fusions, antibody conjugates, single chain antibodies, antibody derivatives, antibody analogues and fragments thereof, respectively. Also included are immunological fragments of an antibody (e.g., a Fab, a Fab', a F(ab')$_2$, or a scFv), irrespective of whether such antibodies are produced, in whole or in part, via immunization, through recombinant technology, by way of in vitro synthetic means, or otherwise. Thus, the term "antibody" is inclusive of those that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transfected to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Such antibodies have variable and constant regions derived from germline immunoglobulin sequences of two distinct species of animals. In certain embodiments, however, such antibodies can be subjected to in vitro mutagenesis (or, when an animal transgenic for human immunoglobulin sequences is used, in vivo somatic mutagenesis) and thus the amino acid sequences of the $V_H$ and $V_L$ regions of the antibodies are sequences that, while derived from and related to the germline $V_H$ and $V_L$ sequences of a particular species (e.g., human), may not naturally exist within that species' antibody germline repertoire in vivo. Unless otherwise indicated, the term "antibody" includes, in addition to antibodies comprising two full-length heavy chains and two full-length light chains, derivatives, variants, fragments, and muteins thereof. In some instances "antibody" may include fewer chains such as antibodies naturally occurring in camelids which may comprise only heavy chains.

As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time. As is known in the art, antibody therapy is commonly administered parenterally (e.g., by intravenous or subcutaneous injection).

The methods of the invention provide for a combination of cytoreductive therapy, including radiation therapy such as local tumor radiation therapy, which serves to kill irradiated cancer cells and releases antigens in close proximity to immune cells in tumors, with immunotherapy (IT), which promotes a local immune response against the irradiated tumor and leads the immune system to respond to sites of metastatic disease outside of the irradiation field.

Radiation therapy is known to enhance antigen presentation and T cell responses to antigen presenting cells. Factors controlling T cell activation by APCs presenting tumor antigen include TCR:MHC interaction, costimulation, and cytokines. Costimulation is determined by a collection of costimulatory and coinhibitory receptor/ligand pairs residing at the cell surfaces of T cells and antigen presenting cells. In order for an effective adaptive immune response to occur and to generate immune memory, costimulation is required. CD28, ICOS, HVEM, CD27, CD30, CD40L, OX40, 4-1BB, TIM-1, and SLAM are major costimulatory receptors.

For example, ionizing radiation (IR) is used to treat about 60% of cancer patients, by depositing energy that injures or destroys cells in the area being treated, and for the purposes of the present invention may be delivered at conventional doses and regimens, or at reduced doses. Radiation injury to cells is nonspecific, with complex effects on DNA. The efficacy of therapy depends on cellular injury to cancer cells being greater than to normal cells. Radiotherapy may be used to treat every type of cancer. Some types of radiation therapy involve photons, such as X-rays or gamma rays. Another technique for delivering radiation to cancer cells is internal radiotherapy, which places radioactive implants directly in a tumor or body cavity so that the radiation dose is concentrated in a small area. A suitable dose of ionizing radiation may range from at least about 2 Gy to not more than about 10 Gy, usually about 5 Gy. A suitable dose of ultraviolet radiation may range from at least about 5 J/m$^2$ to not more than about 50 J/m$^2$, usually about 10 J/m$^2$.

Unlike locally administered adjuvants, costimulation-enhancing therapies such as annexin V can be administered as a single dose intravenously and 'boost' the local response after RT without an invasive procedure. In this manner, annexin V can be used concurrently with local RT directed at an internal tumor target or a single symptomatic metastasis, promote a RT-associated immune response, and generate a systemic (abscopal) immune response.

As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Unless otherwise apparent from the context, all elements, steps or features of the invention can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and Clon-Tech.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in an underlying DNA sequence without affecting the protein sequence. Moreover, due to biological functional equivalency considerations, changes, particularly conservative changes, can be made in protein structure without affecting the biological action in kind or amount. All such modifications are intended to be included within the scope of the appended claims.

Methods

Cancer Immunotherapy

In one aspect, the present invention discloses a method for treating cancer by reducing immunosuppression associated with tumor cell growth. The methods of the invention administer an effective dose of annexin V to block PS on tumor cells, and to thereby disrupt an undesirable interaction between tumor cells and immunoregulatory cells.

In some embodiments the methods of administering annexin V are combined with a second therapy that targets interactions between tumor cells and immunoregulatory cells, e.g. by administering in combination with an antibody that targets an immune checkpoint inhibitor. The combination may provide for an effect on tumor growth or survival that is synergistic relative to the effect of the individual therapies, that is the effect of annexin V or a checkpoint inhibitor as a monotherapy.

Cancer immunotherapy is the use of the immune system to reject cancer. The main premise is stimulating the patient's immune system to attack the malignant tumor cells that are responsible for the disease. This can be either through immunization of the patient, in which case the patient's own immune system is trained to recognize tumor cells as targets to be destroyed, or through the administration of therapeutic agents that reduce immunosuppression, in which case the patient's immune system is recruited to destroy tumor cells.

Since the immune system responds to the environmental factors it encounters on the basis of discrimination between self and non-self, many kinds of tumor cells that arise as a result of the onset of cancer are more or less tolerated by the patient's own immune system since the tumor cells are essentially the patient's own cells that are growing, dividing and spreading without proper regulatory control. In spite of this fact, however, many kinds of tumor cells display unusual antigens that are either inappropriate for the cell type and/or its environment, or are only normally present during the organisms' development. Other kinds of tumor cells display cell surface receptors that are rare or absent on the surfaces of healthy cells, and which are responsible for activating cellular signal transduction pathways that cause the unregulated growth and division of the tumor cell. Despite the potency and specificity of the immune system, vaccination with tumor antigens generally fails to eradicate cancer in mice and humans.

The methods of the present invention allow the bodies innate defense system to act against cancer cells. Methods are provided for treating a subject with a therapeutic dose of an annexin V agent, including without limitation human annexin V protein or an active fragment or derivative thereof. The subject methods include a step of administering a therapeutically effective dose of an annexin V agent to the subject.

The administration of a therapeutically effective dose of an annexin V agent can be achieved in a number of different ways Suitable administration of a therapeutically effective dose can entail administration of a single dose, or can entail administration of doses daily, semi-weekly, weekly, once every two weeks, once a month, annually, etc.

The effective dose in a human may be up to about 50 µg/kg, up to about 100 µg/kg, up to about 250 µg/kg, up to about 500 µg/kg, up to about 750 µg/kg, up to about 1 mg/kg, up to about 1.5 mg/kg, up to about 2 mg/kg, up to about 5 mg/kg, up to about 7.5 mg/kg, up to about 10 mg/kg, up to about 20 mg/kg. The effective dose of annexin V may be combined with other treatment modalities, including without limitation chemotherapeutic drugs, radiation therapy, anti-cancer biologic agents such as monoclonal antibodies directed to tumor antigens, VEGF, etc.; and the like.

In some cases, a therapeutically effective dose is administered as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose, and each subsequent dose can be increased by a particular increment (e.g., by 0.5 mg/kg), or by variable increments, until a therapeutic dose is reached, at which point administration may cease or may continue (e.g., continued therapeutic doses). In some embodiments, administration of a therapeutically effective dose can be a continuous infusion and the dose can altered (e.g., escalated) over time. In some embodiments a combination therapy, e.g. with radiation therapy, an immune checkpoint inhibitor, etc. is also administered.

Dosage and frequency may vary depending on the half-life of the agent in the patient. It will be understood by one of skill in the art that such guidelines will be adjusted for the molecular weight of the active agent. The dosage may also be varied for localized administration, e.g. intratumor, etc., or for systemic administration, e.g. i.m., i.p., i.v., and the like.

The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

The term "cancer" as used herein includes carcinomas, (e.g., carcinoma in situ, invasive carcinoma, metastatic carcinoma) and pre-malignant conditions, i.e. neomorphic changes independent of their histological origin. The term "cancer" is not limited to any stage, grade, histomorphological feature, invasiveness, aggressiveness or malignancy of an affected tissue or cell aggregation. In particular stage 0 cancer, stage I cancer, stage II cancer, stage III cancer, stage IV cancer, grade I cancer, grade II cancer, grade III cancer, malignant cancer and primary carcinomas are included.

The types of cancer that can be treated using the subject methods of the present invention include but are not limited to adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's lymphoma, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squarnous cell or epidermoid carcinoma, bronchial adenoma, choriocarinoma, head and neck cancers, teratocarcinoma, or Waldenstrom's macroglobulinemia.

In a preferred embodiment, the subject method is used to treat a solid tumor, for example, colorectal cancer, lung cancer, liver cancer, breast cancer, prostate cancer, ovarian cancer or pancreatic cancer.

Clinical Efficacy

Tumor growth and disease progression is monitored during and after treatment of cancer via the subject methods of the present invention. Clinical efficacy can be measured by any method known in the art. In some embodiments, clinical efficacy of the subject treatment method is determined by measuring the clinical benefit rate (CBR).

The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD months. In some embodiments, CBR for the subject treatment method is at least about 50%. In some embodiments, CBR for the subject treatment method is at least about 55%, 60%, 65%, 70%, 75%, 80%, 85%, 90%, 95% or more.

Pharmaceutical Compositions.

Suitable annexin V agents can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, the use of an annexin V agent includes use in combination with another therapeutic agent (e.g., another anti-cancer agent). Therapeutic formulations comprising one or more annexin V agents of the invention are prepared for storage by mixing the agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The agent composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The annexin V agent can be administered by any suitable means, particularly parenteral parenteral. Parenteral infusions include intramuscular, intravenous (bollus or slow drip), intraarterial, intraperitoneal, intrathecal, intratumor, or subcutaneous administration.

The annexin V agent need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

An annexin V agent is often administered as a pharmaceutical composition comprising an active therapeutic agent and another pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an anti-CD47 agent or primer agent by non-covalent associations, such as non-covalent bonding or by encapsulation. The nature of the carrier can be either soluble or insoluble for purposes of the invention. Those skilled in the art will know of other suitable carriers for binding anti-CD47 agents and/or primer agents, or will be able to ascertain such, using routine experimentation.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the methods of the invention. Such moieties may be conjugated to the annexin V agent through an acceptable chemical linker or chelation carrier. Positron emitting moieties for use in the present invention include $^{18}$F, which can be easily conjugated by a fluorination reaction with the annexin V agent.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the annexin V agents can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in further optimizing a therapeutic dosage range and/or a priming dosage range for use in humans. The exact formulation, route of administration and dosage can be chosen by the individual physician in view of the patient's condition.

Combination Therapy

In some embodiments, the subject method further comprises administering to a subject in need thereof radiation therapy, an anti-tumor agent, or a pharmaceutically acceptable salt or prodrug thereof. In some embodiments, the anti-tumor agents include but are not limited to antitumor alkylating agents, antitumor antimetabolites, antitumor antibiotics, plant-derived antitumor agents, antitumor organoplatinum compounds, antitumor campthotecin derivatives, antitumor tyrosine kinase inhibitors, monoclonal antibodies, interferons, biological response modifiers, and other agents having antitumor activities, or a pharmaceutically acceptable salt thereof. As used herein, the term "combination therapy" refers to those situations in which a subject is simultaneously exposed to two or more therapeutic regimens (e.g., two or more therapeutic agents). In some embodiments, two or more agents may be administered simultaneously; in some embodiments, such agents may be administered sequentially; in some embodiments, such agents are administered in overlapping dosing regimens.

In some embodiments, the subject method further comprises treating a subject in need thereof one or more of the following therapies in combination with the subject method disclosed herein.

Suitable antineoplastic anti-tumor agents to be used in the present invention include, but are not limited to, alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and anti-metastatic agents.

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents to be used in the present invention can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural antineoplastic agents comprise antimitotic agents, antibiotic antineoplastic agents, camptothecin analogues, and enzymes. Antimitotic agents suitable for use herein include, but are not limited to, vinca alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural antineoplastic agents are the antibiotic antineoplastic agents: Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants. L-asparaginase acts by depriving some cancer cells of L-asparagine by catalyzing the hydrolysis of circulating asparagine to aspartic acid and ammonia.

Hormonal antineoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable for use in the present invention to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 121974, ZD6474, BAY 543-9006, celecoxib, halofuginone hydrobromide, bevacizumab, their analogues, variants, or derivatives.

Differentiating agents inhibit tumor growth through mechanisms that induce cancer cells to differentiate. One such subclass of these agents suitable for use herein includes, but is not limited to, vitamin A analogues or retinoids, and peroxisome prolifeiator-activated receptor agonists (PPARs). Retinoids suitable for use herein include, but are not limited to, vitamin A, vitamin A aldehyde (retinal), retinoic acid, fenretinide, 9-cis-retinoid acid, 13-cis-retinoic acid, all-trans-retinoic acid, isotretinoin, tretinoin, retinyl palmitate, their analogues and derivatives. Agonists of PPARs suitable for use herein include, but are not limited to, troglitazone, ciglitazone, tesaglitazar, their analogues and derivatives.

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies may be comprised of non-human animal (e.g. mouse) and human components, or be comprised of entirely human components ("humanized antibodies"). Examples of monoclonal immunotherapeutic agents suitable for use herein include, but are not limited to, rituximab, tosibtumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraCIM hR3, 2C4, HGS-TR2J, and HGS-ETR2.

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present invention.

Nanometer-sized particles have novel optical, electronic, and structural properties that are not available from either individual molecules or bulk solids. When linked with tumor-targeting moieties, such as tumor-specific ligands or monoclonal antibodies, these nanoparticles can be used to target cancer-specific receptors, tumor antigens (biomarkers), and tumor vasculatures with high affinity and precision. The formulation and manufacturing process for cancer nanotherapy is disclosed in patent U.S. Pat. No. 7,179,484, and article M. N. Khalid, P. Simard, D. Hoarau, A. Dragomir, J. Leroux, Long Circulating Poly(Ethylene Glycol) Decorated Lipid Nanocapsules Deliver Docetaxel to Solid Tumors, Pharmaceutical Research, 23 (4), 2006, all of which are herein incorporated by reference in their entireties.

RNA including but not limited to siRNA, shRNA, microRNA may be used to modulate gene expression and treat cancers. Double stranded oligonucleotides are formed by the assembly of two distinct oligonucleotide sequences where the oligonucleotide sequence of one strand is complementary to the oligonucleotide sequence of the second strand; such double stranded oligonucleotides are generally assembled from two separate oligonucleotides (e.g., siRNA), or from a single molecule that folds on itself to form a double stranded structure (e.g., shRNA or short hairpin RNA). These double stranded oligonucleotides known in the art all have a common feature in that each strand of the duplex has a distinct nucleotide sequence, wherein only one nucleotide sequence region (guide sequence or the antisense sequence) has complementarity to a target nucleic acid sequence and the other strand (sense sequence) comprises nucleotide sequence that is homologous to the target nucleic acid sequence.

MicroRNAs (miRNA) are single-stranded RNA molecules of about 21-23 nucleotides in length, which regulate gene expression miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

Certain RNA inhibiting agents may be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Cand5, Sirna-027, fomivirsen, and angiozyme.

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

Certain protein or small molecule agents can be used in anti-cancer therapy through either direct anti-tumor effects or through indirect effects. Examples of direct-acting agents suitable for use herein include, but are not limited to, differentiating reagents such as retinoids and retinoid derivatives. Indirect-acting agents suitable for use herein include, but are not limited to, agents that modify or enhance the immune or other systems such as interferons, interleukins, hematopoietic growth factors (e.g. erythropoietin), and antibodies (monoclonal and polyclonal).

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

Certain pharmaceutical agents can be used to prevent initial occurrences of cancer, or to prevent recurrence or metastasis. In some embodiments, treatment of cancer with the subject methods is accompanied with the use of chemopreventative agents. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoid acid, 13-cis-retinoid acid, all-trans-retinoic acid, isotretinoin, tretinoid, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylomithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium. An additional example of chemopreventative agents suitable for use in the present invention is cancer vaccines. These can be created through immunizing a patient with all or part of a cancer cell type that is targeted by the vaccination process.

In some embodiments, treatment of cancer with the subject methods is accompanied by administration of pharmaceutical agents that can alleviate the side effects produced by the antineoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoin, their analogues and derivatives. Examples of agents that can treat anemia or thrombocytopenia associated with chemotherapy suitable for use herein include, but are not limited to, erythropoietin, and thrombopoietin.

Kits

Also provided are kits for use in the methods. The subject kits include an annexin v agent, e.g. a wild type or mutant annexin v protein. In some embodiments, the agent is provided in a dosage form (e.g., a therapeutically effective dosage form). In some embodiments, an anti-CD47 agent is provided in two or more different dosage forms (e.g., two or more different therapeutically effective dosage forms). In the context of a kit, an agent can be provided in liquid or sold form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site. The kit may further comprise imaging agents for detection and imaging of PS positive cancer cells suitable for treatment with the methods of the invention.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

In a set of experiments, as shown in FIG. 1, it was found that doses of 2 m/kg of wild type annexin V given as single or divided doses inject intraperitoneally (i.p.) have a significant reduction in tumor growth and even regression with 24 hours of a single dose of protein in 4T1-tumor (syngeneic, poorly differentiated, murine mammary carcinoma) bearing Balb/c mice. Repeat dosing at 2 days enhanced the effect which appeared to taper by 48 to 72 hours.

Figure 2:
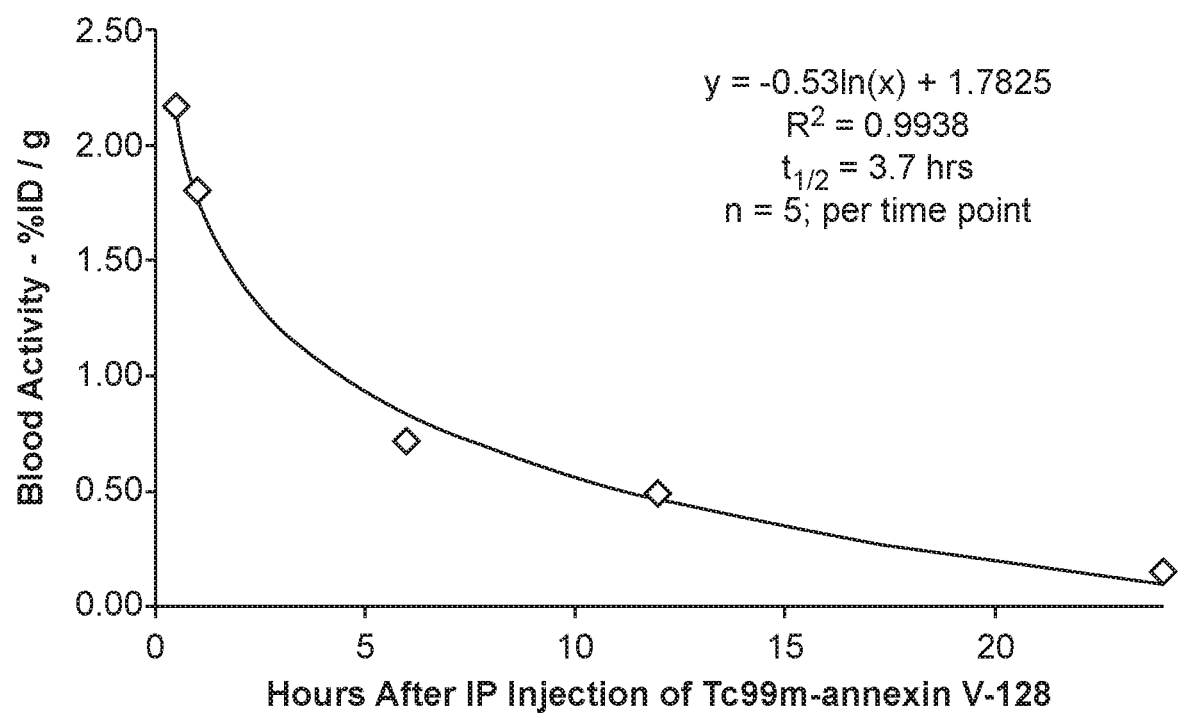
FIG. 2. Blood clearance of Tc99m-annexin. V-128 (1 mg/kg protein per mouse in 0.5 cc normal saline) following ip injection. Blood was obtained via supra-infra-orbital bleeding via capillary tubes while animals were sedated. Data obtained from 5 tumor bearing mice per group (19 days after implantation of 50,000 4T1 cells into the left mammary fat pad). Tumors from the same group of mice were then excised weighed and counted after euthanizing mice at the same time points.
Figure 2:
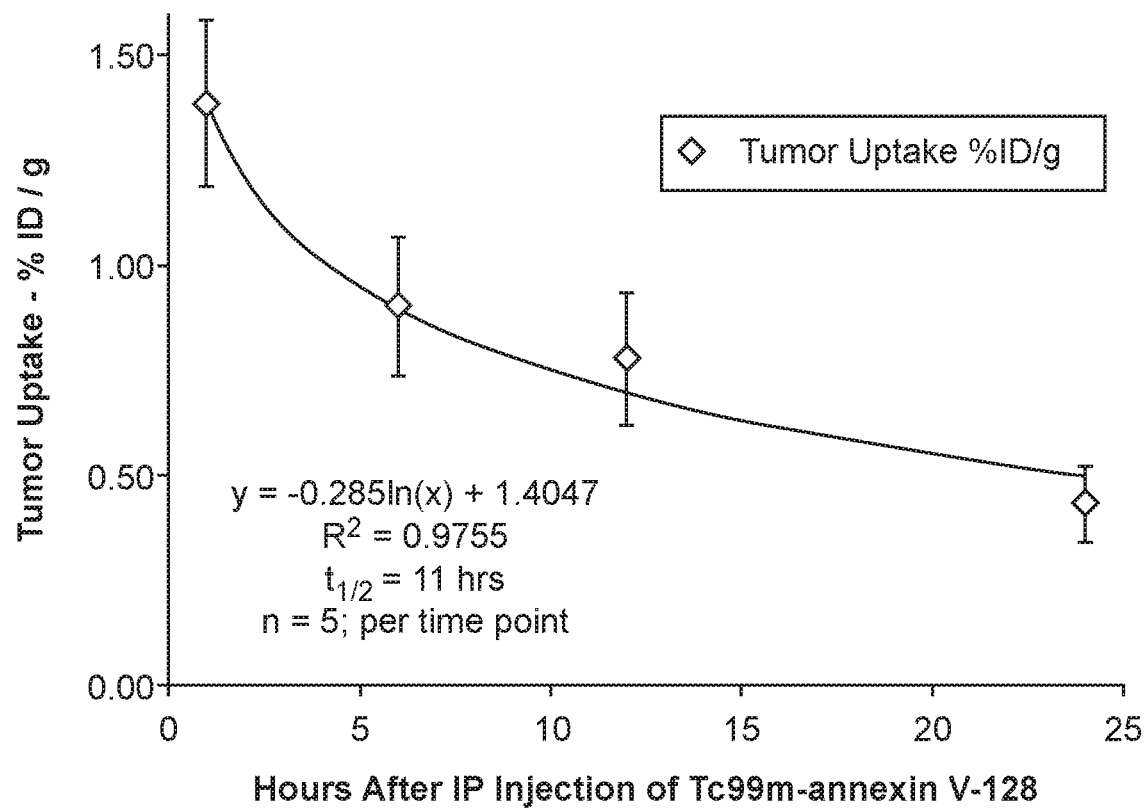

Blood clearance is shown in FIG. 2. The effects of annexin V are likely dependent on the rate of infusion and the prolongation of annexin V in the circulation (ie prolonged blood clearance). Dosing by intraperitoneal injection increases the half-life of annexin V in blood from 8 minutes to 3.5 hours. Similar results can be obtained by administering through a slow intravenous infusion of annexin V over, for example, a 12-24 hour period.

Example 2

Use of Annexin V as a Method to Block Tumor Induced Immunosuppression of the Innate Immune Response A method to reverse PS induced immunosuppression in poorly differentiated triple negative breast tumors is described, using slow continuous infusion of recombinant wild type annexin V at maximal daily NOAEL (no observed adverse event level=2.5 mg/kg/day in rats) dosing over a one week period. rh-annexin V is an endogenous human protein (MW=36,000) which has a high binding affinity for PS. rh-annexin V has been tested extensively as an imaging agent in previous clinical trials with no reported adverse events following two or more intravenous injections of protein in over 300 patients. The anti-tumor immunostimulatory mechanisms of annexin V are independent of other types immunotherapies including PD-1 and CTLA-4 antibodies and synergistic interaction between annexin V with these and other agents is expected. Furthermore, annexin V infusion is may synergistically enhance the recognition of apoptotic tumor following radiation therapy locally as well as sites of disease outside the radiation field.

The lack of immune response to most human tumors can be explained in part by the development of PS mediated peripheral tolerance to specific tumor associated antigens (TAAs) contained within apoptotic tumor cells. Cells undergoing apoptosis normally express high levels of PS which serves as a universal "eat me signal" through which the innate immune system, including NK cells, T-cells and monocytes/macrophages (MDs) recognize and harmlessly remove dying cells without inciting an inflammatory response. However, intermediate and reversible levels of PS exposure below the threshold for phagocytosis, can also be observed on viable tumor cells as well as on metabolically stressed cells or activated T lymphocytes. The presence of high or intermediate levels of PS on the surface of tumor cells and tumor reactive T lymphocytes alone are sufficient suppress the recognition and response to TAAs by both the innate and adaptive immune systems.

The immunosuppressive effects of PS are mediated by a number of newly described immune cell receptors that specifically bind to PS including TIM-4 (T cell immuno-globulin- and mucin domain-containing molecule-4). TIM-4 is a member of the T cell/transmembrane, immunoglobulin, and mucin (TIM) gene family and is exclusively expressed on MDs and dendritic cells (DCs). TIM-4 mediates the phagocytosis of apoptotic cells and can also recognize and respond to intermediate levels of PS exposure on non-apoptotic cells. Both high and intermediate levels of PS on tumor cells and TAA reactive T lymphocytes induce the transition of MDs from an active (M1) to a tolerogenic (M2, TAM=tumor associated macrophage) phenotype. TAMs with an M2 phenotype (↑IL-10 & TGF-β, ↓IL-12), induce the development of tumor-specific T-regs (T cell, regulatory); cells that actively suppress CD8+ (cytotoxic) T cells (CTLs) upon their activation by TAAs. TAMs also prevent DC maturation, abrogate the cross-priming of naïve CD4+ T cells by TAAs presented by DCs, and suppress DC co-stimulatory cell to cell interactions with NK (natural killer T cells). Myeloid derived stem cells or MDSCs are also highly immunosuppressive upon ingestion of or contact with PS+ cells and can inhibit the function of tumor specific CTL cells by inducing the clonal expansion of tumor specific T-regs. MDSCs can also convert naïve CD4+ cells into tumor specific T-regs. The blockade of TAM and MDSC PS mediated-phagocytosis is expected to interfere with the immunosuppressive effects of T-regs on tumor specific CTLs.

Annexin V and murine chimeric PS-binding anti-body (bavituximab) have both been used to increase the antigenicity of tumor cells by blocking PS-dependent recognition by the immune system. Annexin V has also been used to block the phagocytosis of apoptotic tumor cells by Mφs shifting the clearance of dying tumor cells to DCs while also increasing M1 activity (↑IL-1β & TNF-α, ↓TGF-β). Interestingly, blockade of Mφ phagocytosis of apoptotic tumor cells with annexin V did not affect the clearance and processing of dying tumor cells or their TAAs by mature DCs. The delayed clearance of apoptotic tumor cells in response to annexin V blockade of PS mediated phagocytosis also allows time for the onset of secondary necrosis (after an apoptotic cell runs out of ATP) which further heightens the immunogenicity of TAAs. Bavituximab, the murine chimeric form of anti-PS antibody for human use, is currently being tested in several Phase III clinical trials. Unfortunately, bavituximab has been recently found not to bind PS directly but indirectly through its specific binding to beta-2 glycoprotein 1, a serum protein with a limited PS affinity as compared with annexin V. Fully humanized forms of anti-PS antibody with high specificities for PS have also failed to localize to tumor in vivo in several murine models casting doubt on whether targeting tumors with anti-PS directed antibodies regardless of specificity, is a viable therapeutic strategy.

Intratumoral injections of annexin V following tumor irradiation or the addition of annexin V to irradiated tumor cell vaccines greatly enhanced immune responses observed in vivo in several animal models. It has also been recognized that ionizing radiation can reduce tumor growth outside the field of radiation (abscopal effect) leading to the conclusion immune responses in response to RT may contribute to the elimination of cancer cells systematically. RT and PS blocking with systemically administered annexin V can provide a synergistic effect. Lastly, the blockade of PS by the endogenous secretion of annexin V by a genetically engineered neuroblastoma cell line promoted a significant anti-tumor response in an immunocompetent murine tumor model. Furthermore, the self-rejection of annexin V secreting neuroblastoma tumors was found to be T-cell dependent and long lasting in 40% of mice.

Figure 3:
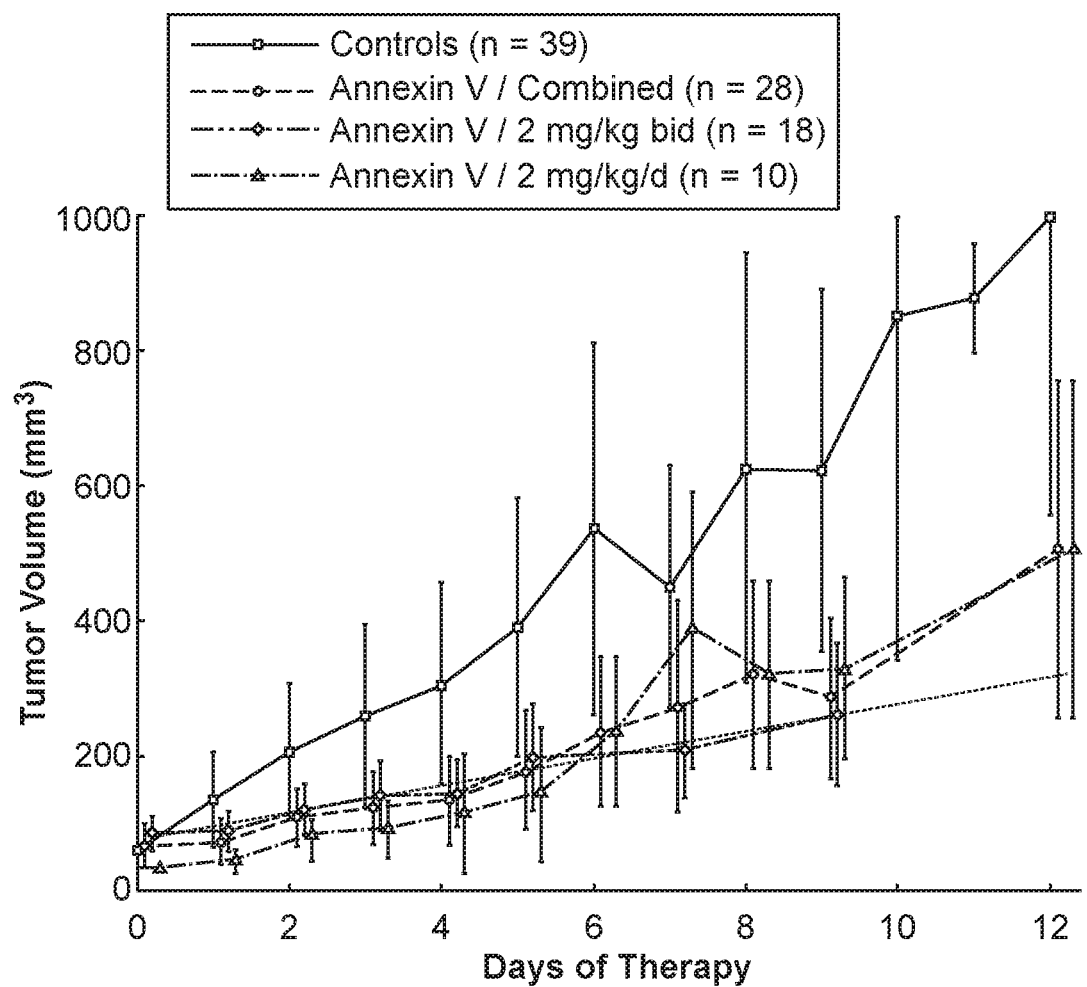
FIG. 3. Annexin V immunotherapy of orthotopic 4T1 axillary fat pad tumors. Young female BALB/c mice 9 to 11 days after direct implantation of 50,000 4T1 cells into the left axillary fat pad received 2 mg/kg/day or 2 mg/kg bid of annexin V injected ip for 8 days.
Figure 4:
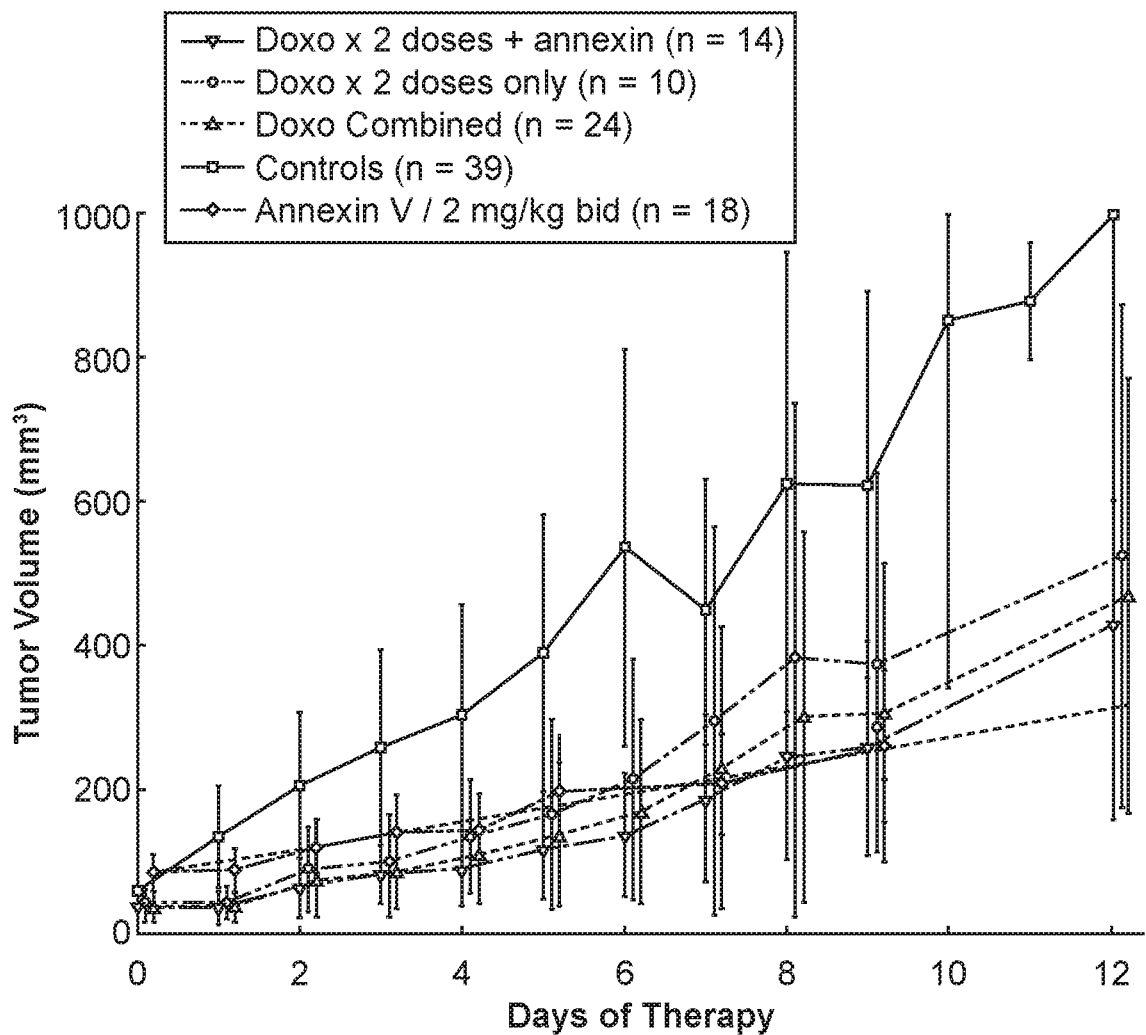
FIG. 4. Doxorubicin and daily i.p. annexin V-immunotherapy of 4T1 axillary fat pad tumors. 4T1 tumor bearing received either; 2 mg/kg/day of wild type annexin V (Theseus Corp.) injected ip for 8 days, doxorubicin 5 mg/kg ip on days 0 and 5, or both.
Figure 5:
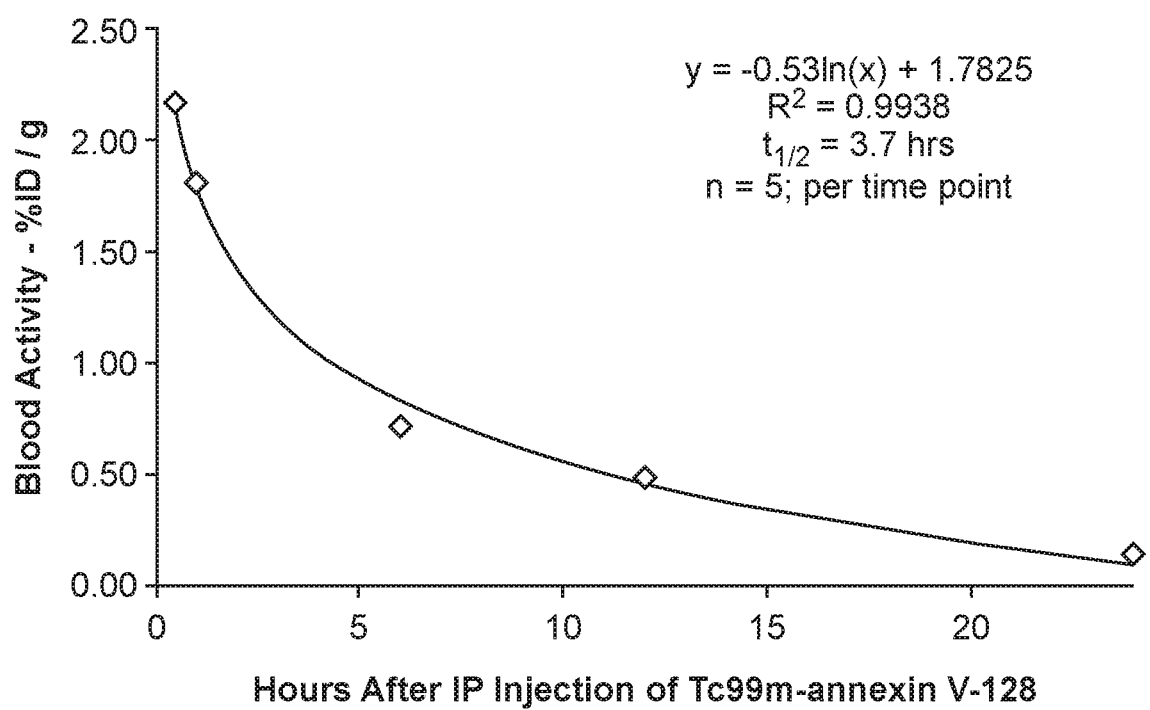
FIG. 5. Blood Clearance of i.p. annexin V-128. Biodistribution assay and clearance studies of 100 uCi of Tc99m-annexin V-128 (1-2 ug protein) was injected ip in 4T1 tumor bearing mice (400 to 600 mm$^3$ in size). Blood samples were drawn weighed and counted over at the time of euthanasia for biodistribution at 30 min, 1 hr, 6 hr, 12 and 24 hrs after ip injection of tracer.
Figure 6:
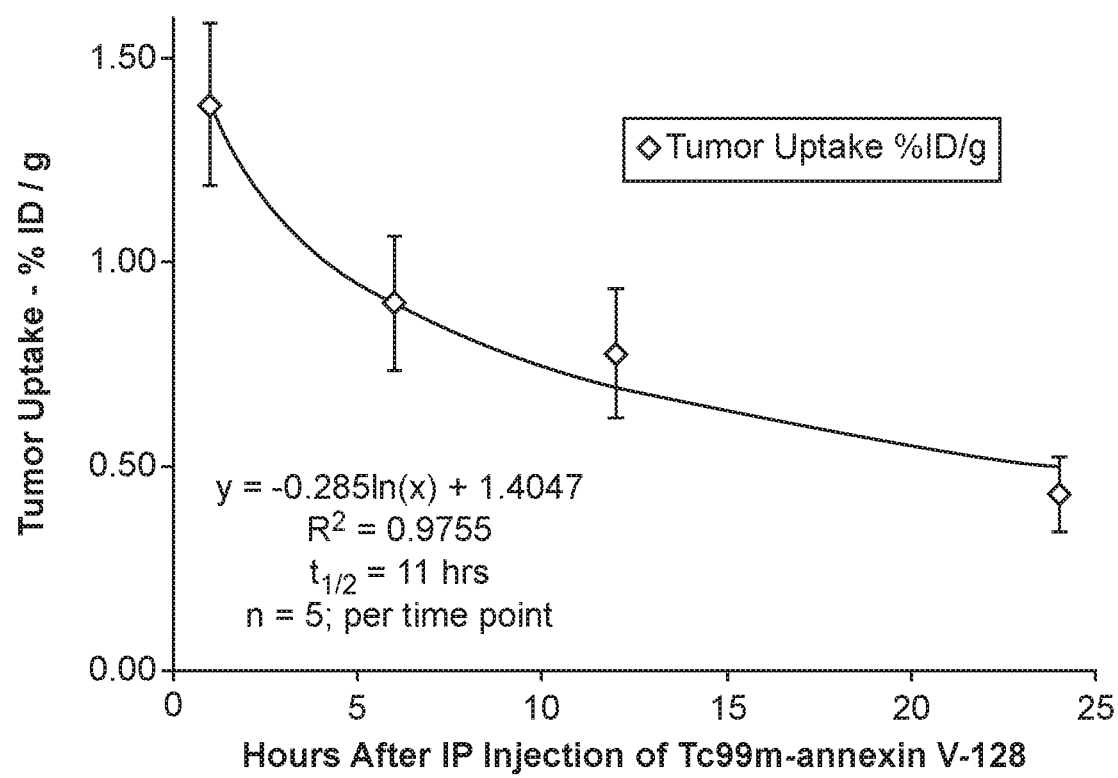
FIG. 6. Tumor $t_{1/2}$ of i.p. annexin V-128. Biodistribution assay and clearance studies of 100 uCi of Tc99m-annexin V-128 (1-2 ug protein) was injected ip in 4T1 tumor bearing mice (400 to 600 mm$^3$ in size). Tumors excised weighed and counted over at the time of euthanasia for biodistribution at 30 min, 1 hr, 6 hr, 12 and 24 hrs after ip injection of tracer.
Figure 7A:
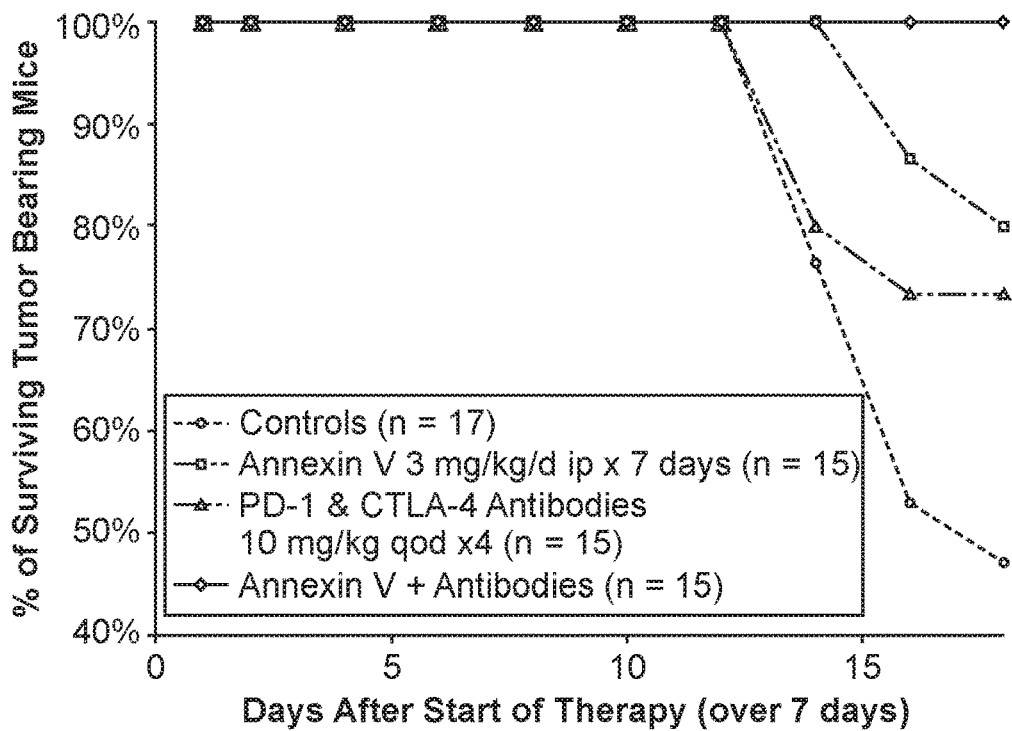
FIG. 7A-7B. Synergistic effect of in vivo combination of annexin V with antibodies for checkpoint inhibitors, effect shown on survival (FIG. 7A) and on tumor growth (FIG. 7B).
Figure 7B:
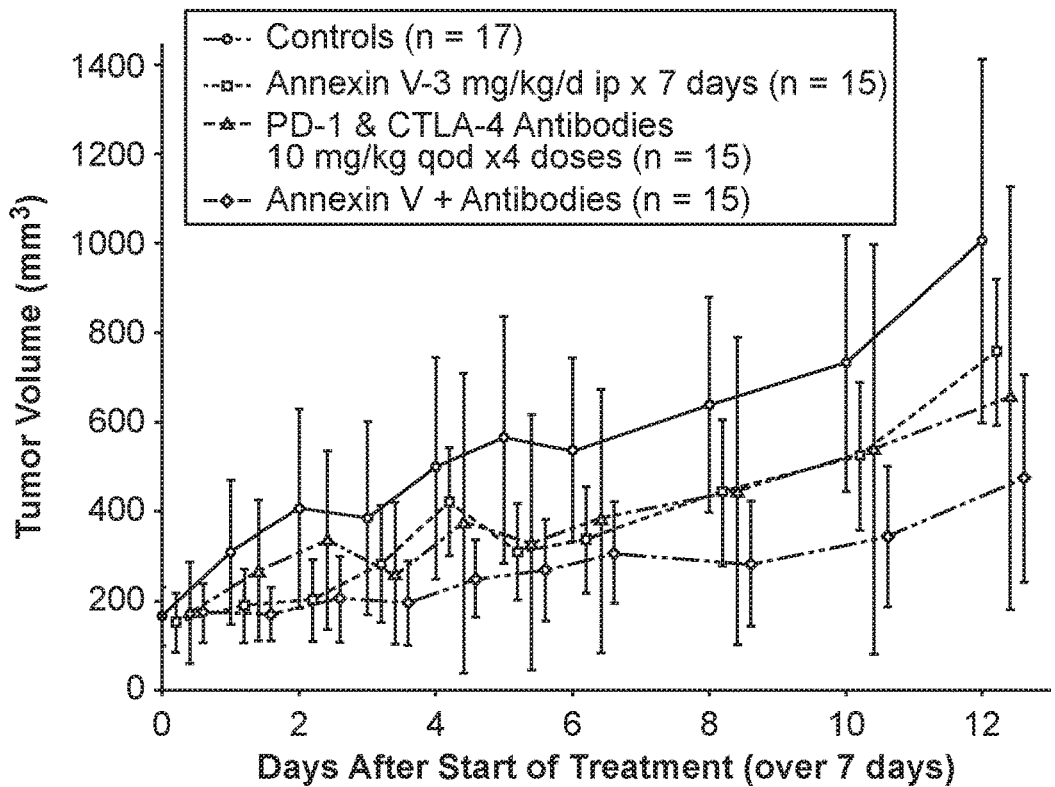

We show herein that wild type annexin V injected intraperitoneally (i.p.) at daily dose of 2 to 4 mg/kg over 8 to 10 days was highly effective at reducing the growth of orthotopic syngeneic 4T1 axillary fat pad tumors in Balb/c mice, a highly aggressive and poorly immunogenic mammary carcinoma, by 60 to 70% as compared with control as shown in FIGS. 3 & 4. We also found that the i.p. route of injection significantly prolonged the circulatory half-life of Tc99m-annexin V-128 to 3.7 hours as well as increasing the residence half-life of Tc99m-annexin V-128 in tumor to well over 11 hours as shown in FIGS. 5 & 6. These data show that annexin V (or annexin V-128) is useful as an adjuvant if paired with other immunologic therapies and administered as a slow intravenous infusion.

Cancer cell lines 4T1 (fast growing, highly metastatic) or JC (slower growing, less aggressive) poorly immunogenic syngeneic mammary carcinomas (both luciferase expressing cell lines) are orthotopically implanted into the left axillary mammary fat pad of young adult female BALB/C mice. After reaching a tumor size of 6-7 mm tumor bearing mice (n=15/group) undergo one week of continuous annexin V infusion (2 mg/kg/d) delivered by intraperitoneally placed osmotic pumps (1007D, Alzet), followed with serial measurements of tumor size and survival compared with untreated controls. In separate groups of mice primary tumors are resected, and mice allowed to recover for one week prior to pump implantation and the start of one week of annexin V infusion. These mice are followed by weekly BLI (bioluminescent imaging) to detect and assess metastatic tumor growth along with survival compared with untreated controls. These experiments are repeated with the addition of immune check point therapy with anti-murine PD-1 and CLTA-4 antibodies (10 mg/kg ip qod×4 doses) to test for synergy with annexin V infusion therapy in mice with either primary or metastatic disease.

The effects of one week of annexin V infusion therapy on primary JC and 4T1 tumors (6-7 mm in size) subcutaneously implanted into the right flank (to facilitate the local delivery of radiation to extremity tumor without irradiating vital organs) is determined. A single dose of 30 Gy is delivered using a small animal X-ray beam (2 cm diameter field) to unanesthetized mice passively restrained in a lead jig. The growth and survival of irradiated primary tumor in annexin V treated mice is compared to irradiated controls. In separate groups of mice primary flank tumor is resected after completing radiation and one week of annexin V infusion therapy and mice followed with weekly BLI to serially monitor metastatic tumor burden along with survival and compare with irradiated mice without annexin V infusion. These experiments are repeated with the addition of anti-murine PD-1 and CLTA-4 antibodies (10 mg/kg ip qod×4 doses) to test for synergy with annexin V infusion therapy in irradiated mice with primary or metastatic disease.

What is claimed is:

1. A method of increasing the immune response to a tumor in an individual, the method comprising:
administering a course of therapy to an individual previously diagnosed with cancer by parenteral administration of an effective dose of up to 5 mg/kg of an active agent consisting of an annexin V protein, wherein the annexin V protein consists of an amino sequence which has at least 95% sequence identity to the amino acid sequence of human annexin V protein in a combination therapy with a second anti-cancer agent, wherein the administering is performed by a route that provides for a circulating half-life of at least about 1 hour.

2. The method of claim 1, wherein the tumor is a carcinoma.

3. A method of increasing the immune response to a tumor positive for surface phosphatidylserine in an individual, the method comprising: administering a course of therapy of an effective dose of from 50 g/kg to 5 mg/kg human annexin V protein to an individual previously diagnosed with cancer, wherein administration is parenteral and provides for a circulating half-life of at least 3 hours, in combination with radiation therapy, and wherein the combination therapy provides for a synergistic effect.

4. The method of claim 1, wherein the effective dose is administered at least twice.

5. The method of claim 1, wherein the combination therapy provides for a synergistic effect.

6. The method of claim 1, wherein the second anti-cancer agent is an immune checkpoint inhibitor, where the combination therapy provides for a synergistic effect.

7. A method of increasing the immune response to a tumor positive for surface phosphatidylserine in an individual, the method comprising:
administering a course of therapy of an effective dose of from 50 µg/kg to 5 mg/kg human annexin V protein wherein administration is by osmotic pump, and provides for a circulating half-life of at least 3 hours, in combination with radiation therapy, wherein the combination therapy provides for a synergistic effect.

8. The method of claim 1, wherein the tumor is positive for expression of surface Phosphatidylserine.

9. The method of claim 8, wherein the presence of a tumor positive for surface expression of Phosphatidylserine is determined by imaging with an annexin V agent.

10. The method of claim 1, wherein the annexin V protein consists of an amino sequence which has at least 99% sequence identity to the amino acid sequence of wild-type human annexin V.

11. The method of claim 1, wherein the annexin V protein is a recombinant annexin V protein.

12. A method of increasing the immune response to a tumor positive for surface phosphatidylserine in an individual, the method comprising: administering to an individual previously diagnosed with cancer an effective dose of up to 5 mg/kg of an active agent consisting of an annexin V polypeptide, wherein the annexin V polypeptide consists of an amino sequence which has at least 95% sequence identity to the amino acid sequence of human annexin V protein, by parenteral administration providing for a circulating half-life of at least 3 hours, in a combination therapy with an immune checkpoint inhibitor, wherein the combination therapy provides for a synergistic effect.

13. The method of claim 12, further comprising:
administering to the individual radiation therapy.

* * * * *